United States Patent [19]
Fairhurst et al.

[11] Patent Number: 6,034,078
[45] Date of Patent: *Mar. 7, 2000

[54] THIENOBENZODIAZEPINE COMPOUNDS

[75] Inventors: John Fairhurst, Basingstoke; Terrence Michael Hotten, Farnborough; David Edward Tupper, Reading, all of United Kingdom; David Taiwai Wong, Indianapolis, Ind.

[73] Assignees: Eli Lilly and Company Limited, Basingstoke, United Kingdom; Eli Lilly and Company, Indianapolis, Ind.

[ * ] Notice: This patent issued on a continued prosecution application filed under 37 CFR 1.53(d), and is subject to the twenty year patent term provisions of 35 U.S.C. 154(a)(2).

[21] Appl. No.: 08/886,847

[22] Filed: Jul. 1, 1997

Related U.S. Application Data

[63] Continuation of application No. 08/335,431, Nov. 7, 1994, abandoned, which is a continuation-in-part of application No. 08/068,007, May 27, 1993, abandoned.

[30] Foreign Application Priority Data

| May 29, 1992 | [GB] | United Kingdom | .................. 9211379 |
| Apr. 30, 1993 | [GB] | United Kingdom | .................. 9309025 |

[51] Int. Cl.[7] .......................... A61K 31/55; C07D 495/04
[52] U.S. Cl. ............................. 514/220; 540/557
[58] Field of Search .............. 540/557; 514/220

[56] References Cited

U.S. PATENT DOCUMENTS

| 3,951,981 | 4/1976 | Safir ........................................ 540/557 |
| 4,115,568 | 9/1978 | Chakrabarti et al. ................. 514/220 |
| 4,725,615 | 2/1988 | Coates et al. ............................ 514/397 |
| 5,051,516 | 9/1991 | Chakrabarti et al. ................. 548/194 |
| 5,114,949 | 5/1992 | Gueremy et al. ....................... 514/320 |
| 5,229,382 | 7/1993 | Chakrabarti et al. ................. 540/557 |
| 5,561,127 | 10/1996 | Tehim et al. ............................. 514/211 |
| 5,602,121 | 2/1997 | Fu ........................................... 540/557 |

FOREIGN PATENT DOCUMENTS

| 454436 | 10/1991 | European Pat. Off. . |
| 2325381 | 4/1977 | France . |

OTHER PUBLICATIONS

Medline Abstract for Ongini et al, *Neuroscience Letters*, 82(2) p206–210 (1987).
Saxena, *Pharmac. Ther.* 66, p 339–368 (1995).
Chakrabarti et al., *J. Med. Chem.*, 23, 878–884 (1980).
Schmutz et al Chem. Abstracts, 80, No. 3562 (Jan. 7, 1984).
Barnes, J. M. *Neuroscience Biobehavioural Review*, 16:107–113.
Costall, B. Scand. *J. Gastroenterology* 25:769–787 (1990).
*Dorland's Medical Dictionary* 1045 (27th ed. 1988).
Fuller, R. W. *Biology of Serotongergic Transmission*, (John Wiley & Sons Ltd., 1982) p. 221–247.
Tupper, D. E., "The Pharmacology of Some Novel 10–Substituted Derivatives of Olanzapine", poster presented at Neuroscience Meeting, Washington, D.C., Nov. 7 through 12, 1993.
Waddinlton, *Gen. Pharmacol.* 19: 55–60 (1988).

*Primary Examiner*—Emily Bernhardt
*Attorney, Agent, or Firm*—Arleen Palmberg; MacCharri Vorndran-Jones

[57] ABSTRACT

Pharmaceutical compounds of the formula

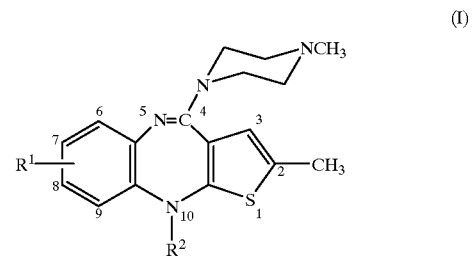

in which $R^1$ is hydrogen or halo, and $R^2$ is $C_{1-10}$ alkyl, $C_{2-10}$ alkenyl, $C_{2-10}$ alkynyl, $C_{3-6}$ cycloalkyl optionally substituted by 1 to 3 $C_{1-4}$ alkyl groups, $C_{3-6}$ cycloalkyl-$C_{1-4}$ alkyl in which the cycloalkyl group is optionally substituted by 1 to 3 $C_{1-4}$ alkyl groups, or optionally substituted phenyl-$C_{1-4}$ alkyl; or a salt thereof. Such compounds are useful for treating a disorder of the central nervous system which is associated with the modulation of a 5-$HT_3$ receptor.

11 Claims, No Drawings

THIENOBENZODIAZEPINE COMPOUNDS

This application is a continuation of application Ser. No. 08/335,431, filed on Nov. 7, 1994, now abandoned which is a continuation-in-part of application Ser. No. 08/068,007, filed on May 27, 1993, now abandoned.

This invention relates to novel organic compounds and their use as pharmaceuticals.

Certain thienobenzodiazepine compounds useful in the treatment of disorders of the central nervous system are described in British Patent 1 533 235 and in European Patent Publication 0 454 436.

The compounds of the present invention have the following formula

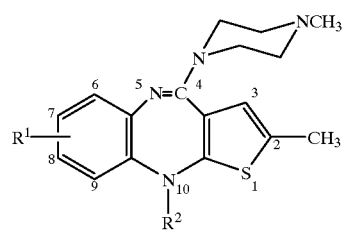

(I)

in which $R^1$ is hydrogen or halo, and $R^2$ is $C_{1-10}$ alkyl, $C_{2-10}$ alkenyl, $C_{2-10}$ alkynyl, $C_{3-6}$ cycloalkyl optionally substituted by 1 to 3 $C_{1-4}$ alkyl groups, $C_{3-6}$ cycloalkyl-$C_{1-4}$ alkyl in which the cycloalkyl group is optionally substituted by 1 to 3 $C_{1-4}$ alkyl groups, or optionally substituted phenyl-$C_{1-4}$ alkyl; or salt thereof.

These compounds are active in experimental screens for testing activity on the central nervous system, and the results indicate their usefulness in the treatment of a wide range of disorders of the central nervous system.

In the above formula $R^1$ can be halo and the halo substituent is preferably fluoro or chloro. The halo atom is preferably attached at the 7-position. When $R^2$ is $C_{1-10}$ alkyl, it can be straight or branched chain, such as, for example, methyl, ethyl, propyl, isopropyl, butyl, isobutyl, pentyl and octyl. A $C_{2-10}$ alkenyl group includes, for example, vinyl, prop-2-enyl, but-3-enyl, pent-4-enyl and oct-7-enyl. A $C_{2-10}$ alkynyl group includes, for example, prop-2-ynyl, but-3-ynyl, pent-4-ynyl and oct-7-ynyl. A $C_{3-6}$ cycloalkyl-$C_{1-4}$ alkyl group is a cycloalkyl group such as, for example, cyclopropyl, cyclobutyl, cyclopentyl or cyclohexyl, attached to $C_{1-4}$ alkyl, and a preferred example is cyclopropylmethyl. The $C_{3-6}$ cycloalkyl group can be substituted with 1 to 3 $C_{1-4}$ alkyl substituents, especially methyl. An optionally substituted phenyl group is phenyl or phenyl substituted with one or more, preferably one to three substituents selected from, for example, $C_{1-4}$ alkyl, especially methyl, $C_{1-4}$ alkoxy, especially methoxy or ethyoxy, hydroxy, nitro, cyano, halo, especially chloro or fluoro, trihalomethyl, especially trifluoromethyl, carboxy or $C_{1-4}$ alkoxycarbonyl. A preferred example of phenyl-$C_{1-4}$ alkyl is benzyl.

A particular group of compounds according to formula (I) is one in which $R^1$ is hydrogen or halo, and $R^2$ is $C_{1-4}$ alkyl, $C_{2-4}$ alkenyl, $C_{2-4}$ alkynyl, $C_{3-6}$ cycloalkyl-$C_{1-4}$ alkyl or optionally substituted phenyl-$C_{1-4}$ alkyl.

A further and preferred group of compounds according to formula (I) is one in which $R^1$ is hydrogen or halo, and $R^2$ is $C_{3-10}$ alkyl, $C_{3-10}$ alkenyl or $C_{3-10}$ alkynyl. Preferably $R^1$ is hydrogen, and preferably $R^2$ is $C_{3-10}$ alkyl, especially $C_{3-8}$ alkyl (more especially $C_3$ or $C_4$ alkyl and particularly propyl and isopropyl).

Another preferred group of compounds are those in which $R^2$ is $C_{1-6}$ alkyl. A further preferred group of compounds are those in which $R^2$ is $C_{3-6}$ alkyl. Compounds wherein $R^2$ is $C_{1-2}$ alkyl are especially preferred for selectivity at the D-1 receptor which is greater than at the 5-$HT_3$ receptor.

It will be understood that salts of the compounds of the invention can be prepared and such salts are included in the invention. They can be any of the well known acid addition salts. Preferably the salts are pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicyclic, o-acetoxybenzoic, or organic sulphonic, 2-hydroxyethane sulphonic, toluene-p-sulphonic, or naphthalene-2-sulphonic acid.

If a phenyl nucleus on an $R^2$ substituent bears an acid function, base salts can be derived, for example, from ammonium hydroxide and alkali and alkaline earth metal hydroxides, carbonates and bicarbonates, as well as salts derived from aliphatic and aromatic amines, aliphatic diamines an dhydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium, sodium and lithium salt forms are preferred.

In addition to pharmaceutically-acceptable salts, other salts are included in the invention. They may serve as intermediates in the purification of compounds or in the preparation of other, for example pharmaceutically-acceptable, salts, or are useful for identification, characterisation or purification.

The invention also includes a process for preparing compounds of formula (I), which comprises alkylating the anion (at the 10-position) of a compound of the formula:

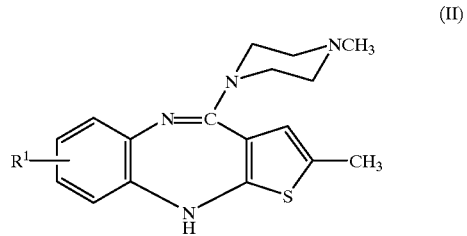

(II)

The reaction can be carried out according to well-known procedures using conventional alkylating agents of the formula $R^2X$ where X is a leaving group such as, for example, halo, especially chloro or bromo or $C_{1-4}$ alkylsulphonate, and a suitable base such as n-butyl lithium or sodium hydride. Preferably a reaction temperature of from −70° C. to +80° C., and an organic solvent such as, for example, tetrahydrofuran or dimethylformamide, are employed.

Alkylating agents of formula $R^2X$ are well-known and compounds of formula (II) can be made according to methods described in British Patent 1 533 235 and European Patent Publication 0 454 436.

As mentioned above, the compounds of the invention have useful central nervous system activity. This activity is indicated by models using well-established procedures. For example, the compounds are active in in vitro binding assays designed to measure the degree of binding to neuronal receptors. The compounds are active at the dopamine D-1 receptor as indicated by an $IC_{50}$ of less than 1 μM in the $^3$H-SCH23390 (Billard, W. et al. Life Sciences 35 1885 (1984)) binding assay. Certain compounds of this invention selectively modulate the D-1 receptor with greater affinity than the D-2 receptors. Especially preferred compounds having selective affinity for the D-1 receptor include those wherein $R^2$ is $C_{1-4}$ alkyl. Particularly preferred $C_{1-4}$ alkyl groups are ethyl and methyl. Further particularly preferred $C_{1-4}$ alkyl groups are n-butyl and n-propyl. The compounds also have an antimuscarinic-anticholinergic activity.

Furthermore, the compounds are active at serotonin receptors. For example, some of the compounds, those in which $R^1$ is hydrogen and $R^2$ is $C_{3-8}$ alkyl, (especially $C_3$ and $C_4$ alkyl, and particularly n-propyl and n-butyl) show a high level of activity on $5-HT_3$ receptors, as measured in the test described by Wong D. T. et al., European Journal of Pharmacology 166 (1989) 107–110. They also possess a degree of selectivity for these receptors over $5-HT_1$ and $5-HT_2$ receptors.

The compounds are also active in standard in vivo tests predictive of antipsychotic activity. They antagonised apomorphine-induced climbing behaviour in mice (Moore N. A. et al. Psychopharmacology 94 (2), 263–266 (1988), and 96, 539 (1988). The compounds also inhibit a conditioned avoidance response in rats.

Such tests indicate that the compounds are a potential neuroleptic with relaxant, anxiolytic or anti-emetic properties, and are useful in treating psychotic conditions such as schizophrenia, schizophreniform diseases and acute mania. At lower doses the compounds are indicated for use in the treatment of mild anxiety states. Furthermore, preferred compounds which have high levels of activity at the $5-HT_3$ receptors, are also indicated for use in treating depression, memory deficit such as abnormal loss of memory, migraine, pain, and drug abuse, for example the undesired consumption of drugs such as alcohol, morphine, nicotine or haloperidol. They are also of potential use in treating anxiety disorders such as major anxiety and panic disorder.

The compounds of the invention are effective over a wide dosage range, the actual dose administered being dependent on the condition being treated. For example, in the treatment of adult humans, dosages of from 0.5 to 30 mg, preferably from 0.1 to 20 mg, per day may be used. A once-a-day dosage is normally sufficient, although divided doses may be administered. For treatment of psychotic disorders a dose range of from 2 to 15 mg, preferably 2.5 to 10 mg per day is suitable, whereas for mild anxiety states a lower dosage range, such as from 0.1 to 5 mg, preferably 0.5 to 1 mg, may be more appropriate. In choosing a suitable regimen for patients suffering from psychotic illness it may frequently be necessary to begin with a dosage of from 2 to 15 mg per day and when the illness is under control to reduce to a dosage as low as from 0.5 to 1 mg per day.

The compounds of the invention may be administered orally or by injection and, for this purpose, it is usually employed in the form of a pharmaceutical composition.

Accordingly the invention includes a pharmaceutical composition comprising as active ingredient a compound of formula (I) or a pharmaceutically-acceptable acid addition salt thereof, associated with a pharmaceutically-acceptable carrier. In making the compositions of the invention conventional techniques for the preparation of pharmaceutical compositions may be used. For example, the active ingredient will usually be mixed with a carrier, or diluted by a carrier, or enclosed within a carrier which may be in the form of a capsule, sachet, paper or other container. When the carrier serves as a diluent, it may be solid, semi-solid or liquid material which acts as a vehicle, excipient or medium for the active ingredient. The active ingredient can be adsorbed on a granular solid container, for example in a sachet. Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxy-benzoate, talc, magnesium stearate or mineral oil. The compositions of the invention may, if desired, by formulated so as to provide quick, sustained or delayed release of the active ingredient after administration to the patient.

Depending on the method of administration, the compositions may be formulated as tablets, capsules, injection solutions for parenteral use, suspensions or elixirs for oral use or suppositories. Preferably the compositions are formulated in a dosage unit form, each dosage containing from 0.1 to 20 mg, more usually 0.5 to 10 mg, of the active ingredient.

A preferred formulation of the invention is a capsule or tablet comprising 0.1 to 20 mg or 0.5 to 10 mg of active ingredient together with a pharmaceutically-acceptable carrier therefor. A further preferred formulation is an injection which in unit dosage form comprises 0.1 to 20 mg or 0.5 to 10 mg of active ingredient together with a pharmaceutically-acceptable diluent therefor. A type of injection formulation that is also desirable is a sustained release formulation for intra-muscular injection, in which case, a unit dose may preferably contain up to 100 mg.

The invention is illustrated by the following Examples.

EXAMPLE 1

2,10-Dimethyl-4-(4-methyl-1-piperazinyl)-10H-thieno-[2,3-b][1,5]benzodiazepine

A solution of 2-methyl-4-(4-methyl-1-piperazinyl)-10H-thieno[2,3-b][1,5]benzodiazepine (3.1 g) (European Patent Publication 0 454 436) in dry tetrahydrofuran (distillated from sodium/benzophenone) was stirred and cooled to −70° C. Tetramethylethylenediamine (1.16 g) was added followed by n-butyllithium (6.25 ml, 0.6M solution), keeping the temperature below −60° C. The deep red solution was stirred for 15 minutes and then methyl iodide (1.42 g) was added. The reaction was allowed to attain room temperature, during which time the red colour discharged. Water was added and the product extracted with ethyl acetate. The solvent was washed with water, dried and evaporated to dryness under reduced pressure. The product was purified by chromatography on Florisil using ethyl acetate as eluent and crystallised from acetronitrile to give the title compound, m.p. 126–128° C.

Similarly prepared from the same starting material were:
10-Ethyl-2-methyl-4-(4-methyl-1-piperazinyl)-10H-thieno [2,3-b][1,5]benzodiazepine m.p. 125–127° C.
2-Methyl-4-(4-methyl-1-piperazinyl)-10-(prop-2-enyl)-10H-thieno[2,3-b][1,5]benzodiazepine m.p. 110–112° C.
2-Methyl-4-(4-methyl-1-piperazinyl)-10-(prop-2-ynyl)-10H-thieno[2,3-b][1,5]benzodiazepine m.p. 155–156° C.
10-Benzyl-2-methyl-4-(4-methyl-1-piperazinyl)-10H-thieno[2,3-b][1,5]benzodiazepine m.p. 188–190° C. (as hydrochloride salt).
10-Butyl-2-methyl-4-(4-methyl-1-piperazinyl)-10H-thieno [2,3-b][1,5]benzodiazepine m.p. 235–237° C. (as hydrochloride salt).
2-Methyl-4-(4-methyl-1-piperazinyl)-10-(2-methyl-propyl)-10H-thieno[2,3-b][1,5]benzodiazepine m.p. 238–240° C. (as hydrochloride salt).

2-Methyl-4-(4-methyl-1-piperazinyl)-10-pentyl-10H-thieno[2,3-b][1,5]benzodiazepine m.p. 210–212° C. (as hydrochloride salt).

2-Methyl-4-(4-methyl-1-piperazinyl)-10-octyl-10H-thieno[2,3-b][1,5]benzodiazepine m.p. 208–210° C. (as hydrochloride salt).

Similarly prepared from 7-fluoro-2-methyl-4-(4-methyl-1-piperazinyl)-10H-thieno[2,3-b][1,5]benzodiazepine (British Patent 1 533 235) were:

7-Fluoro-2,10-dimethyl-4-(4-methyl-1-piperazinyl)-10H-thieno[2,3-b][1,5]benzodiazepine m.p. 145–147° C.

10-Ethyl-7-fluoro-2-methyl-4-(4-methyl-1-piperazinyl)-10H-thieno[2,3-b][1,5]benzodiazepine m.p. 128–130° C.

7-Fluoro-2-methyl-4-(4-methyl-1-piperazinyl)-10-propyl-10H-thieno[2,3-b][1,5]benzodiazepine m.p. 67–70° C.

10-Cyclopropylmethyl-7-fluoro-2-methyl-4-(4-methyl-1-piperazinyl)-10H-thieno[2,3-b][1,5]benzodiazepine m.p. 50–52° C.

7-Fluoro-2-methyl-4-(4-methyl-1-piperazinyl)-10-(prop-2-enyl)-10H-thieno[2,3-b][1,5]benzodiazepine m.p. 108–111° C.

7-Fluoro-2-methyl-4-(4-methyl-1-piperazinyl)-10-(prop-2-ynyl)-10H-thieno[2,3-b][1,5]benzodiazepine m.p. 50–55° C.

10-Benzyl-7-fluoro-2-methyl-4-(4-methyl-1-piperazinyl)-10H-thieno[2,3-b][1,5]benzodiazepine m.p. 65–67° C.

EXAMPLE 2

2-Methyl-10-(1-methylethyl)-4-(4-methyl-1-piperazinyl)-10H-thieno[2,3-b][1,5]benzodiazepine To a solution of 2-methyl-4-(4-methyl-1-piperazinyl)-10H-thieno[2,3-b][1,5]benzodiazepine (3.12 g) in dry dimethylformamide (50 ml) was added sodium hydride (0.63 g, 50% dispersion). The reaction mixture was stirred for 30 minutes at room temperature, then 30 minutes at 60–70° C. The reaction was cooled to 40° C., isopropyl bromide (1.13 ml) added and left for one hour. Water was added and the reaction extracted with ethyl acetate, washed with water, dried and evaporated under reduced pressure. Chromatography using 2% methanol/dichloromethane and flash silica gave the title compound, m.p. 120–121° C. Similarly prepared from the same starting material were:

2-Methyl-4-(4-methyl-1-piperazinyl)-10-propyl-10H-thieno[2,3-b][1,5]benzodiazepine m.p. 122–123° C.

10-Cyclopropylmethyl-2-methyl-4-(4-methyl-1-piperazinyl)-10H-thieno[2,3-b][1,5]benzodiazepine m.p. 105–106° C.

The following formulations can be made using an active compound of the invention.

EXAMPLE 3

A tablet formulation is made by granulating the active with appropriate diluent, lubricant, disintegrant and binder and compressing

| Compound of the invention | 5.0 mg |
|---|---|
| Magnesium stearate | 0.9 mg |
| Microcrystalline cellulose | 75.0 mg |
| Povidone | 15.0 mg |
| Starch, directly compressible | 204.1 mg |

EXAMPLE 4

An aqueous injection of active is prepared as a freeze-dried plug, for reconstitution in a suitable, sterile diluent before use (to a total volume of 10 ml).

| Compound of the invention | 20.0 mg |
|---|---|
| Mannitol | 20.0 mg |
| N Hydrochloric acid and/or N sodium hydroxide to adjust pH to 5–5.5. | |

EXAMPLE 5

A controlled release injection for intramuscular injection is formed from a sterile suspension of micronised active in an oleaginous vehicle.

| Compound of the invention | 65.0 mg |
|---|---|
| Aluminium stearate | 0.04 mg |
| Sesame oil | 2 ml |

EXAMPLE 6

A formulation is prepared by blending the active with starch and silicone starch, and filling it into hard gelatine capsules.

| | Per 290 mg capsule |
|---|---|
| Compound of the invention | 2.5 mg |
| Starch flowable with 0.96% silicone 220 | 217.5 mg |
| Starch flowable | 70.0 mg |

We claim:

1. A compound of the formula:

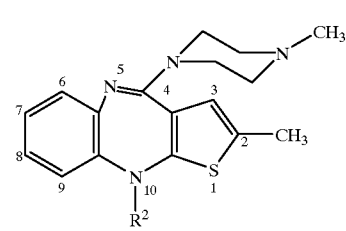

(I)

in which $R^2$ is $C_{3-5}$ alkyl, $C_{3-5}$ alkenyl or $C_{3-5}$ alkynyl, or a salt thereof.

2. A compound of the formula:

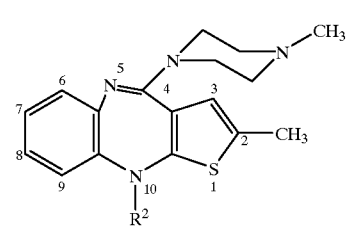

(I)

in which $R^2$ is $C_3$ alkenyl or $C_3$ alkynyl.

3. A compound according to claim 1, in which $R^2$ is $C_{3-5}$ alkyl.

4. A compound according to claim 3 in which $R^2$ is $C_{3-4}$ alkyl.

5. A compound according to claim 4 in which $R^2$ is propyl.

6. A compound according to claim 4 in which $R^2$ is butyl.

7. A pharmaceutical formulation comprising a compound according to claim 1, or a pharmaceutically-acceptable salt thereof, together with a pharmaceutically-acceptable diluent or carrier therefor.

8. A method for treating memory deficit, comprising administering an effective amount of a compound of claim 3, or a pharmaceutically acceptable salt thereof, to a person suffering from memory deficit.

9. A method for treating schizophrenia, which comprises administering an effective amount of a compound of claim 3, or a pharmaceutically acceptable salt thereof, to a subject suffering from schizophrenia.

10. A method for treating migraine, which comprises administering an effective amount of a compound of claim 3, or a pharmaceutically acceptable salt thereof, to a subject suffering from migraine.

11. A method for treating drug abuse, which comprises administering an effective amount of a compound of claim 3, or a pharmaceutically acceptable salt thereof, to a subject suffering from drug abuse.

* * * * *